US00PP30091P3

(12) United States Plant Patent
Wezelenburg, Jr.

(10) Patent No.: US PP30,091 P3
(45) Date of Patent: Jan. 15, 2019

(54) ***ACER* TREE NAMED 'JWW7'**

(50) Latin Name: *Acer palmatum*
Varietal Denomination: JWW7

(71) Applicant: Jan-Willem Wezelenburg, Jr., Hazerswoude-Dorp (NL)

(72) Inventor: Jan-Willem Wezelenburg, Jr., Hazerswoude-Dorp (NL)

(73) Assignee: JAN-WILLEM WEZELENBURG BOSKOOP B.V., Hazerswoude-Dorp (NL)

( * ) Notice: Subject to any disclaimer, the term of this patent is extended or adjusted under 35 U.S.C. 154(b) by 0 days.

(21) Appl. No.: 15/731,649

(22) Filed: Jul. 12, 2017

(65) Prior Publication Data

US 2018/0027714 P1 Jan. 25, 2018

(30) Foreign Application Priority Data

Jul. 20, 2016 (QZ) ..... PBR 2016/1821

(51) Int. Cl.
*A01H 5/00* (2018.01)
*A01H 5/12* (2018.01)
*A01H 5/04* (2018.01)

(52) U.S. Cl.
USPC ..... Plt./224
CPC ..... *A01H 5/12* (2013.01); *A01H 5/04* (2013.01)

(58) Field of Classification Search
USPC ..... Plt./216, 224
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Acer palmatum*, 'JWW7', that is characterized by its vigorous growth habit, and its young shoots that are purple-brown in color, summer foliage that is medium green in color and second summer shoots that are red in color.

2 Drawing Sheets

Botanical classification: *Acer palmatum.*
Variety denomination: 'JWW7'.

BACKGROUND OF THE INVENTION

The present invention relates to a new and distinct cultivar of *Acer palmatum*, and will be referred to hereafter by its cultivar name, 'JWW7'. 'JWW7' is a deciduous tree grown for use as a landscape plant.

The new cultivar originated as a chance seedling growing in a production field of *Acer palmatum* at a nursery in Hazerswoude-Dorp, The Netherlands in May of 2013. The parent plants are unknown as the field was planted with seeds collected and pooled from various unnamed open pollinated plants of *Acer palmatum.*

Asexual reproduction of the new cultivar was first accomplished by grafting by the Inventor in Hazerswoude-Dorp, The Netherlands in the summer of 2013. Asexual propagation of 'JWW7' by grafting has shown that the unique features of the new cultivar are stable and are reproduced true to type in successive generations.

SUMMARY OF THE INVENTION

The following traits have been repeatedly observed and represent the characteristics of the new cultivar. These attributes in combination distinguish 'JWW7' as a new and unique cultivar of *Acer.*

1. 'JWW7' exhibits a vigorous growth habit.
2. 'JWW7' exhibits young shoots that are purple-brown in color, summer foliage that is medium green in color and second summer shoots that are red in color.

'JWW7' be compared to the *Acer* cultivars 'Osakazuki' (not patented) and 'Nicholsonii' (not patented). 'Osakazuki' is similar to 'JWW7' in being the same overall plant shape. 'Osakazuki' differs from 'JWW7' in having leaves that are 5-lobed and in producing second summer shoot leaves that are green in color. 'Nicholsonii' is similar to 'JWW7' in having a vigorous growth habit and a similar mature foliage color. 'Nicholsonii' differs from 'JWW7' in having a less upright plant habit, spring leaves that are olive green to olive brown in color and second summer shoot leaves that are green in color.

BRIEF DESCRIPTION OF THE DRAWINGS

The accompanying colored photographs illustrate the overall appearance and distinct characteristics of a two-year-old plant of the new cultivar as grown in a greenhouse in a 19-cm circular container in Hazerswoude-Dorp, The Netherlands.

Figure 1:
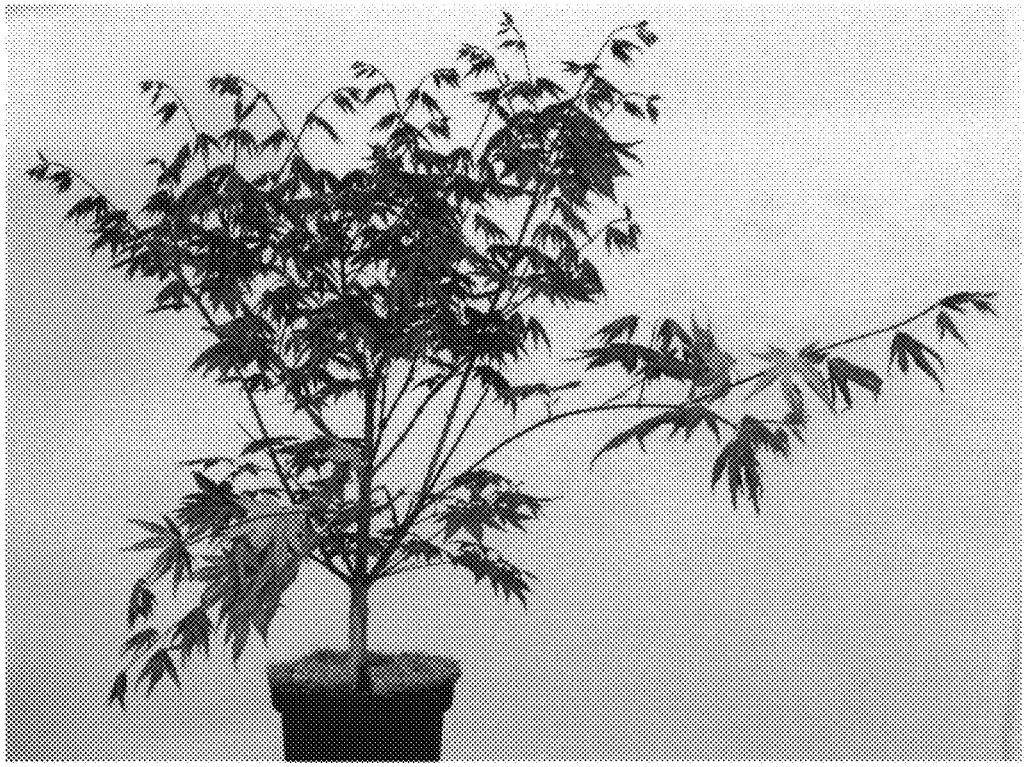
FIG. 1 provides an overall view of the foliage and plant habit of 'JWW7'.
Figure 2:
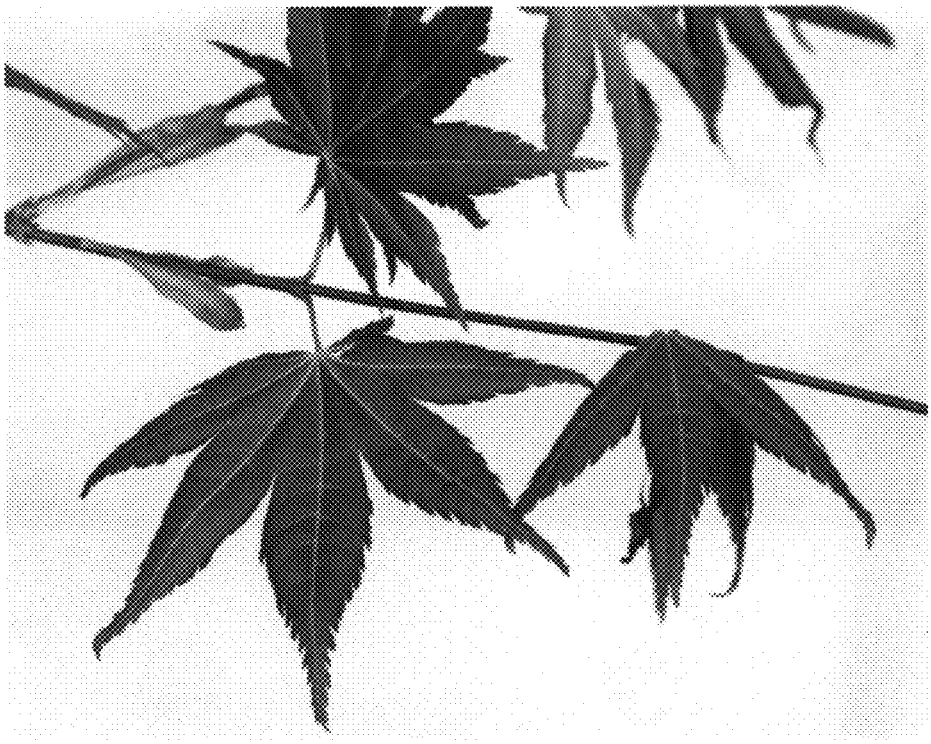

The photograph in FIG. 2 provides a close-up view of the young foliage of 'JWW7'.

Figure 3:
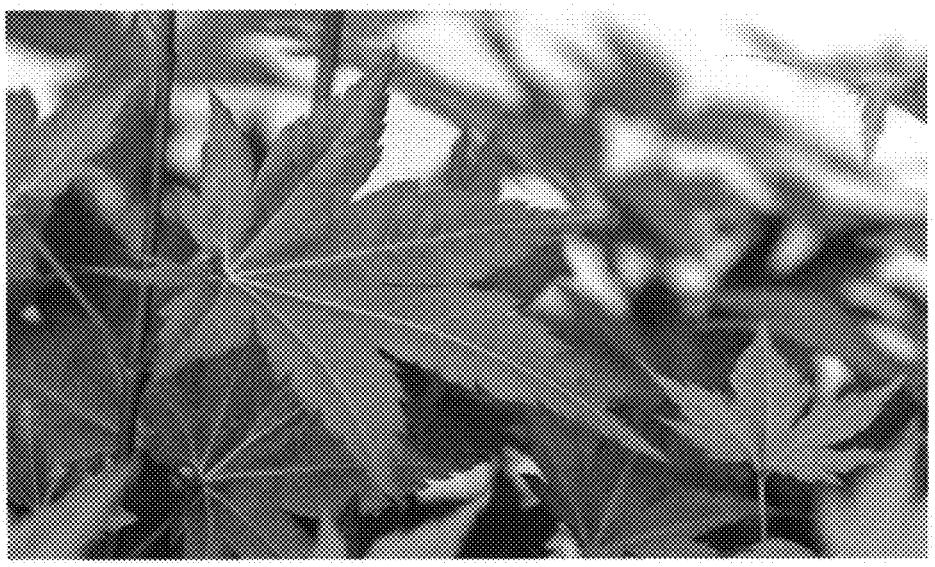

The photograph in FIG. 3 provides a close-up view of the mature foliage of 'JWW7'.

The colors in the photographs may differ slightly from the color values cited in the detailed botanical description, which accurately describe the colors of the new *Acer.*

DETAILED BOTANICAL DESCRIPTION

The following is a detailed description of a two-year old plant of the new cultivar as grown in a greenhouse in a 19-cm container in April in Hazerswoude-Dorp, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Deciduous tree.

*Plant habit.*—Very broad spreading and upright.

*Height and spread.*—An average of 72 cm in height and 105 cm in spread as a 2 year-old plants as grown in a 19-cm container, an average of 500 cm in height and 350 cm in width as a mature plant in the landscape.

*Hardiness.*—At least in U.S.D.A. Zones 6 to 9.

*Diseases.*—No susceptibility or resistance to diseases has been observed.

*Root description.*—Fibrous, freely branched.

*Propagation.*—Grafting.

*Crop time.*—An average of 14 months to produce a young plant.

*Growth rate.*—Vigorous.

Branch description:

*Stem shape.*—Round.

*Stem color.*—Young shoots; between 183A and 185A, young branches; between 146C and 147A, flushed with a blend of 183A to 183B and 185A, mature branches; between 146C and 148A, upper surface flushed with 165A, older branches and bark; between 146A and 148A and 144A, bark is 199D.

*Stem size.*—Lateral branches; average of 34.5 cm in length and 4 mm in width, main stem; average of 30 cm in length and 2 cm in width at soil line.

*Stem surface.*—Texture and luster; young branches; slightly glossy, glabrous, mature branches; slightly glossy and lightly covered with lenticels, an average of 5 to 10 lenticels per square cm, 1 mm in length, 0.5 mm in width, 156D in color, main branch older bark; slightly glossy and slightly exfoliating and bark-like, densely covered with lenticels, an average of 15 to 30 lenticels per square cm, 1.5 mm in length, 1 mm in width, 156D in color.

*Stem strength.*—Strong.

*Stem aspect.*—An average angle of 45° to vertical.

*Internode length.*—An average of 5.2 cm.

*Branching.*—Well-branched, 1 main stem and 15 secondary branches per main branch.

Foliage description:

*Leaf shape.*—Palmately lobed, orbicular in outline.

*Leaf division.*—Simple.

*Leaf base.*—Hastate.

*Leaf apex.*—Narrow acute.

*Leaf fragrance.*—None.

*Leaf venation.*—Palmate, upper surface color is N144A and 148A, lower surface color is 144C and 148A.

*Leaf quantity.*—An average of 14 (7 pairs) per lateral branch.

*Leaf margins.*—Palmately 7-lobed, lobe margins serrate to bi-serrate, sinus depth medium to deep, sinus orientation is convergent.

*Leaf arrangement.*—Opposite.

*Leaf aspect.*—Flat to very slightly convexed, leaves in an average angle of 40° to lateral branch.

*Leaf attachment.*—Petiolate.

*Leaf surface.*—Texture of both surfaces glabrous and smooth, luster of both surfaces is matte.

*Leaf size.*—Up to 8.5 cm in length and 9 cm width.

*Leaf color.*—Young leaves upper surface; between 166A and 183A, flushed with 185A, young leaves lower surface; 177B, mature and fall leaves upper surface; a blend of 148A, 144A and 137A, flushed with a blend of 185A and 166A, predominately flushed with a blend of 185A and 166A at the margins, mature and fall leaves lower surface; 146C to 146D.

*Petioles.*—Up of 3 cm in length and 1 mm in width, texture is smooth and glabrous with a matte luster, upper surface color 180A to 180B, fading to 179C, lower surface 150C.

*Stipules.*—None.

Inflorescence description: None observed to date.

Fruit and seed: None observed to date.

It is claimed:

1. A new and distinct cultivar of *Acer palmatum* tree named 'JWW7' as herein illustrated and described.

* * * * *